United States Patent
Petersen

(10) Patent No.: US 8,622,914 B2
(45) Date of Patent: Jan. 7, 2014

(54) INTEGRATED ULTRASOUND TRANSMITTER WITH CASCODE TRIMMING

(75) Inventor: David A. Petersen, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 124 days.

(21) Appl. No.: 13/024,581

(22) Filed: Feb. 10, 2011

(65) Prior Publication Data

US 2012/0209120 A1    Aug. 16, 2012

(51) Int. Cl.
*A61B 8/14*    (2006.01)

(52) U.S. Cl.
USPC .............................. 600/459; 73/584

(58) Field of Classification Search
USPC .................... 600/459; 327/108, 109, 112
See application file for complete search history.

(56) References Cited

U.S. PATENT DOCUMENTS

| 6,380,766 | B2 * | 4/2002 | Savord ........................ 327/108 |
| 7,588,539 | B2 | 9/2009 | Petersen |
| 7,659,756 | B2 | 2/2010 | Walker |
| 2006/0098059 | A1 * | 5/2006 | Ohguro et al. ................. 347/72 |
| 2009/0007414 | A1 * | 1/2009 | Phelps et al. .................... 29/594 |

* cited by examiner

*Primary Examiner* — Long V. Le
*Assistant Examiner* — Nicholas Evoy

(57) ABSTRACT

Transmitters and waveform generators are provided for ultrasound imaging. Low-voltage transistors are connected in cascode with the high-voltage transistors used to generate the ultrasound pulses. The low-voltage transistors trim the high-voltage transistors, adjusting the drive strength of the high-voltage transistors. By trimming, the rise and fall time of the pulses generated by the high-voltage transistors may be more closely matched.

9 Claims, 2 Drawing Sheets

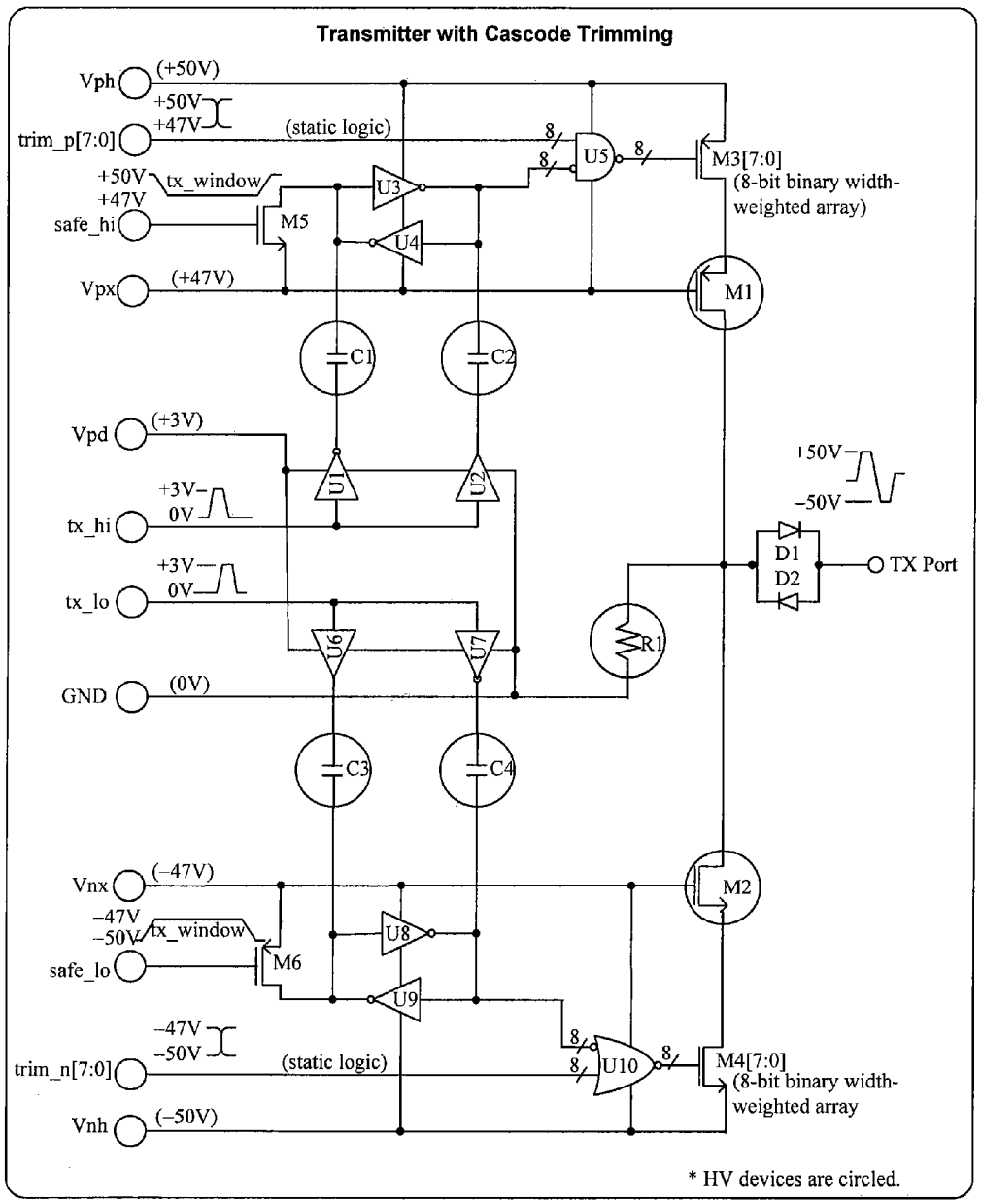

INTEGRATED ULTRASOUND TRANSMITTER WITH CASCODE TRIMMING

BACKGROUND

The present embodiments relate to ultrasound imaging transmitters. In particular, a ultrasound pluser is used to generate an ultrasound wave for scanning a patient.

Ultrasound transmitters include waveform generators for generating ultrasound waveforms. Unipolar or bipolar pulsed waves may be generated using one or more transistors. The transistors are switched on and off, connecting high voltage sources (+/−) or ground to an output. The connections generate a square wave.

Ultrasound transmitters may be integrated in an application specific integrated circuit. For bipolar operation, both P-type and N-type transistors are used, one for generating positive portion of the waveform and the other for generating the negative portion of the waveform. Since different types of transistors are used, the rise and fall times of the portions may be mismatched. For harmonic or contrast agent imaging, this mismatch may result in noise or an artifact. Mirror symmetric positive and negative portions are desired.

BRIEF SUMMARY

By way of introduction, the preferred embodiments described below include methods, transmitters, waveform generators, and systems for ultrasound imaging. Low-voltage transistors are connected in cascode with the high-voltage transistors used to generate the ultrasound pulses. The low-voltage transistors trim the high-voltage transistors, adjusting the drive strength of the high-voltage transistors. By trimming, the rise and fall time of the pulses generated by the high-voltage transistors may be more closely matched.

In a first aspect, a bipolar transmitter is provided for generating bipolar ultrasound pulses with first and second high-voltage transistors. This switching pulser is improved by including a first low-voltage transistor connectable between a positive voltage source and a first source terminal of the first high-voltage transistor and a second low-voltage transistor connectable between a negative voltage source and a second source terminal of the second high-voltage transistor. The first and second low-voltage transistors are operable to adjust drive strengths of the first and second high-voltage transistors, respectively. The first and second high-voltage transistors comprise first and second gate terminals connectable with positive and negative gate voltage sources, respectively, such that the first and second low-voltage transistors are operable control an on/off state of the first and second high-voltage transistors, respectively, with the positive and negative gate voltages sources comprising constant, during transmission, voltages connected to the first and second gates.

In a second aspect, a method is provided for generating an ultrasound waveform. A drive strength of a high-voltage transistor is trimmed with a low-voltage transistor connected in cascode. The ultrasound waveform is generated with the high-voltage transistor as trimmed by the low-voltage transistor.

In a third aspect, a waveform generator is provided for ultrasound imaging. A first field effect transistor (FET) is operable over at least a ten volt range. A second FET connects in cascode with the first FET. An output connects with the first FET. The first FET is operable to generate a transmit pulse on the output.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 3 is a circuit diagram of an example embodiment of the transmitter of FIG. 2.

DETAILED DESCRIPTION OF THE DRAWINGS AND PRESENTLY PREFERRED EMBODIMENTS

In one embodiment, rise and fall times are trimmed to match each other and/or rise and fall times of other pulses. The trimming is programmed By changing the trimming for generating different ultrasound waveforms, the matching may occur over a wide range of transmitter outputs. Trimming is provided by an array of low-voltage transistors in cascode with a single pair of high-voltage transistors. Selection of trim codes directly varies the drive strengths of the high-voltage transistors. Low-voltage transistors are much smaller than high-voltage transistors, so the circuit is smaller than where additional high-voltage devices are provided. Multiple high-voltage devices for the positive side and multiple high-voltage devices for the negative side are not used. Digital control is used for trimming, so that precise analog control of the high-voltage transistor gate drivers is not needed.

The drive strength of a high-voltage transistor is adjusted by a low-voltage transistor connected in cascode. The state (i.e., on/off pulsing) of the high-voltage transistor is controlled by only turning on and off the low-voltage transistor rather than controlling the gate signal. For refined trimming, an array of low-voltage transistors is used. This array of low-voltage transistors is controlled by digital signals. The array controls the drive strength over a wide range of output voltages. The same adjustable transmitter may be used for both pulse wave (e.g., 10-200 volt peak-to-peak) and continuous wave (e.g., 1-20, such as 1-5, volt peak-to-peak) outputs. For bipolar operation, a complementary pair of such adjustable strength devices matches overall rise and fall characteristics of an integrated ultrasound transmitter.

Low voltage transistors (e.g., LV CMOS FETs) to do the switching and high voltage transistors (e.g., HV FETs) shield the low voltage transistors from exposure to high voltage while letting the low voltage transistors be responsible for turning the switch on and off and for determining the strength when on.

Figure 1:
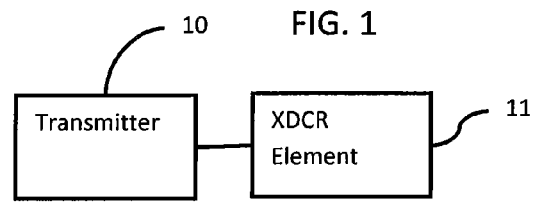
FIG. 1 is a block diagram of an ultrasound waveform generator according to one embodiment.

FIG. 1 shows one embodiment of a waveform generator for ultrasound imaging. The waveform generator is a transmitter 10. The transmitter 10 connects to a transducer element 11. The transmitter 10 generates a waveform, such as a bipolar or unipolar square wave. The waveform may not be an exact square wave as the transistors of the transmitter have rise and fall times which are not instantaneous. The transducer element 11 converts the electrical waveform into acoustic energy. By providing the waveform generator for each of a plurality of channels and corresponding elements 11, phased array scanning may be provided. One waveform generator may include one or more transmitters 10, such as having 64, 128, 256, or 288 transmitters 10.

Figure 2:
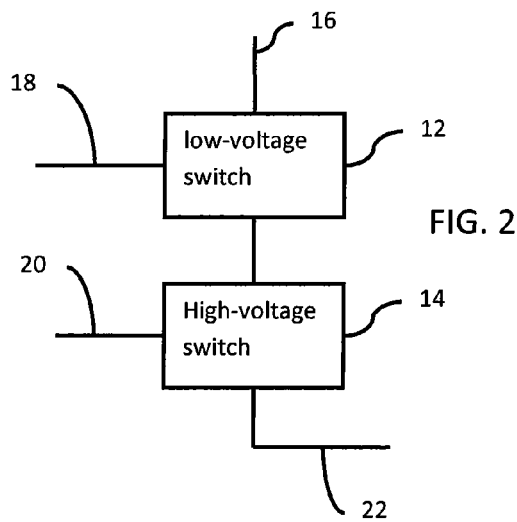
FIG. 2 is a block diagram of one embodiment of a transmitter with cascode trimming.

FIG. 2 shows one example of two switches 12, 14 operable as a transmitter for generating ultrasound pulses. An ultrasound pulse is a pulse at an ultrasound frequency. The pulse is a single positive or negative pulse. A chain of such pulses may be generated. For bipolar operation, positive and negative pulses are generated in sequence. For generating bipolar ultrasound pulses, two additional switches of FIG. 2 are provided for a bipolar transmitter.

The switches 12, 14 are integrated in a same circuit or chip. For example, an application specific integrated circuit includes one or more of the transmitters shown in FIG. 2. The different components are formed using the same or different processes on the same semiconductor substrate, such as using CMOS processes.

The integrated circuit is used within an ultrasound system. For example, a coaxial cable connects the output 22 to a transducer element 11 of an ultrasound array. In another embodiment, the integrated circuit is positioned within a transducer housing for connection to a multi-dimensional array, such as a transesophageal array. By integrating both high and low voltage switches 12, 14 in the same integrated circuit, a small transmit beamformer for use in a probe is provided. The same semiconductor substrate is used for both the high voltage and low voltage switches 12, 14. Multiple transmitters, such as 64, 128, 256, or other number of transmitters may be integrated into the same chip or application specific integrated circuit.

The application specific integrated circuit and/or the chip may have various inputs and outputs. For example, traces are provided to receive signals or voltages from positive and negative voltage sources, the positive and negative gate voltage sources, gate control signals for the low-voltage switches 12, positive pulse and negative pulse activation signals (e.g., binary indication of on or off for a given high-voltage switch 14), and/or fail safe control. One or more outputs may be provided for outputting the ultrasound signals. Any combination of inputs and outputs may be used.

FIG. 3 shows a bipolar circuit diagram of an example of the transmitter of FIG. 2. The circuit includes high voltage switches M1/M2 (14), low voltage switch arrays M3/M4 (12), and/or other components. The circuit diagram is of an integrated circuit with various inputs and the output TX Port (22). A high positive voltage power supply connector Vph (16), a high negative voltage power supply connector Vnh (16), negative and positive trim control connectors trim-n and trim-p (18), positive and negative gate voltages Vnx and Vpx (20), ground GND, logic power supply connector Vpd, safety override control connectors safe-hi and safe-lo, and pulse control connectors tx_hi and tx_low. Additional, different or fewer inputs and outputs may be provided. For example, the trim controller is included on the integrated circuit, so separate inputs are not provided for trim control. As another example, the trim control is also used as the pulse control.

In one embodiment of FIG. 2, the low-voltage switch 12 is a low voltage transistor, such as a 3.3V FET. The low voltage transistor may be manufactured using CMOS processes. The high-voltage switch 14 is a high-voltage FET (a non-CMOS device). The pair of devices provides a positive or negative pulse. Another pair of switches 12 and 14 may provide the other of negative or positive pulse. For example, FIG. 3 shows two pairs of the low- and high-voltage switches M3/M4 and M1/M2 connected with a same output TX Port for generating a bipolar waveform. The low-voltage switch arrays 12 are connected in cascode for adjusting the strength of the respective high-voltage switches 14 so that the high-voltage switches 14 have matched or similar rise and fall times. The bipolar waveform may be more mirror-symmetric.

The positive and negative voltage connectors 16 are for connection with or connect to positive and negative voltage sources, respectively. The voltages provided at the positive and negative voltage connectors 16 are supplied by fixed or variable voltage sources. Other voltage regulators may be provided, such as providing for a voltage supply or regulation integrated within the integrated circuit. Any voltage may be provided, such as +/−10-200 volts for pulse wave operation or 1-20 volts for continuous wave operation.

The positive and negative gate voltage connectors 20 are for connection with or connect to positive and negative voltage sources, respectively. The same sources as the positive and negative voltage sources may be used, such as with a voltage divider to provide gate voltages less than the positive and negative voltages. Alternatively, separate sources are provided. The voltages provided at the positive and negative gate voltage connectors 20 are supplied by fixed or variable voltage sources. Other voltage regulators may be provided, such as providing for a voltage supply or regulation integrated within the integrated circuit.

The positive and negative gate voltages are fixed, DC, or otherwise constant during transmission. The gate voltages may be different for different operation, such as being about 2-4 (e.g., 3) volts less or more than the positive and negative voltages at the connectors 16. This voltage difference is selected to avoid overloading the low-voltage switches 12.

The high-voltage switches 14 are field effect transistors (FETs). For example, a P-type FET or N-type FET are used. In the embodiment of FIG. 3, the positive high-voltage switch M1 is a P-type FET, and the negative high-voltage switch M2 is a N-type FET. The high voltage switches 14 form a waveform generator and are complimentary field effect transistors, but may include other types of transistors or switches. Each of the high voltage switches 14 may be of a same or different type of switch or transistor.

The high voltage switches 14 are operable with at least 10 or more volts, such as allowing for a 10 to 200 volt supply at the input connector 16. A lower voltage may be provided, such as a voltage lower than the highest voltage for operating with continuous waves. For example, each of the high voltage switches 14 is sized to have a gate oxide and other associated dimensions for operating with a 10 or 200 volt power supply. The drain-to-source resistance in the "on" state may be of any of various values, such as being 500 or less ohms The high voltage switches 14 are integrated on a same chip or within a same circuit.

The high-voltage switches each have a gate, source, and drain. The sources are connected with the drains of the low-voltage switches 12. The gate connects with the gate voltage connector 20. The drain connects with the output 22. Other connections, such as with or without intervening components, may be used.

The high-voltage switch 14 is configured to generate a transmit pulse with a relatively constant voltage at the gate. The voltage at the gate is constant during the on/off operation of the high-voltage switch 14. The difference in the gate and source voltages activates or not the high-voltage switch 14. The low-voltage switch 12 may be used to create or not a sufficient difference between the source voltage and the gate voltage, such as being no difference for "off" and being at least 1, 2, 3, or greater volts difference for "on." In the embodiment of FIG. 3, the gate voltages are 47 and −47 volts and the positive and negative voltages at the connectors Vph and Vnh are 50 and −50 volts, but other absolute voltages and/or difference in voltages may be used. The voltage difference is greater than the threshold-on voltage of the high-voltage switch 14. In one embodiment, the high-voltage switch 14 turns on and off only by the low-voltage switch 12 connected in cascode turning on and off. In alternative embodiments, a combination of change in the gate and change in the source voltage or change only in the gate voltage turns the high voltage switch 14 on and off. The degree that high-voltage switch 14 turns on (its "strength") depends on the difference in its source and gate voltage.

The high voltage switches 14 are operable to generate a transmit pulse on the output 22. The high voltage switch or switches 14 form a switching pulser. More complex pulsers may be provided using a greater number of switches. The high voltage switches 14 generate transmit pulses. By turning on, then off, a pulse is generated. Turning on the switch 14 causes the voltage provided by the trimming low-voltage switch 12 to connect to the output 22. The low-voltage switch 12 connects the voltage from the connector 16, as adjusted by the trimming, to the output 22. This creates a substantially square wave pulse. Substantially accounts for the rise time and fall time as well as any overshoot. By turning on, then off repetitively, a pulse train is generated. Either a single pulse or multiple pulse train type of waveform may be used.

The high voltage switch 14 with the low voltage switch 12 (the transmitter 10) operates for or with different supply voltages. The voltages supplied at the supply voltage connector 16 and the gate voltage connector 20 may be different for different modes of operation. For example, a supply voltage of 10-50 volts is provided for continuous wave scanning. A supply voltage of 50-200 volts is provided for pulsed wave scanning. The supply voltage sets the amplitude of the output waveform. The peak voltage on the output 22 for the generated transmit pulses may be different depending on the supply voltage. The gate voltage of the high voltage switch 14 is at a constant ratio or difference from the supply voltage. The difference between the gate voltage and the supply voltage applied to the low voltage switch 12 is less than five, four or other operation voltage regardless of continuous or pulse wave operation.

The integrated circuit 10 is operable to generate either pulsed or continuous waves. The output 22 connects directly or indirectly with a transducer element 11 for converting the generated waveform into acoustic energy. The continuous or pulsed waveforms are bipolar waveforms, but unipolar or more complex waveforms may be generated for either or both of continuous or pulsed wave operation.

The continuous and pulsed waveforms generated by the high voltage switch 14 are output on the output 22. The output 22 is a signal trace, a connector, conductor or other device for electronically connecting the integrated circuit on the semiconductor chip with external components. The output TX Port is connected with the two high voltage switches M1/M2 in the embodiment of FIG. 3. The output 22 allows connection to a given ultrasound transducer element 11 or other component.

The low voltage switch 12 is a complementary field effect transistor, but other switches or transistors may be used. For example, the low voltage switch 12 is a Low voltage transistor, such as a low voltage FET. In the embodiment of FIG. 3, the low voltage switches M3/M4 may be of a same type or different type of switches from each other. Each low voltage switch 12 has a turn-on threshold of less than 6 volts, such as a 1 to 2 volt threshold. Greater or lesser threshold voltages may be provided. The low voltage switches 12 have a thinner oxide layer at the gate or other differences in dimensions for operation with exposure to a lesser voltage than the high voltage switches 14. In one embodiment, the low voltage switch 12 is smaller than the high voltage switch 14. For example, the low voltage switch 12 is operable with voltage supplies or differences across the gate and source less than 10 volts, such as voltages of 2.5 to 12 volts. The drain-to-source resistance of the low voltage switch 12 is much lower, such as ten times smaller than the drain to source resistance of the high voltage switch 14. For example, the resistance of the low voltage switch 12 is 50 ohms or less. Lesser resistance is provided by having a thinner oxide and a shorter channel. Greater resistances may be provided with a similar or different ratio of resistances from the high voltage switch 14 to the low voltage switch 12.

The low voltage switch 12 connects between the voltage source, such as the positive voltage source connector 16 and the source of the high voltage switch 14. The connection may be connectable, such as associated with a fixed connection or a connection that may be connected or removable (e.g., a chip for mounting on a board or with a switch provided between the devices). In the embodiment of FIG. 3, the low voltage switches M3/M4 are connectable between the sources of the high voltage switches M1/M2 and the respective positive and negative voltage supply connectors Vph and Vnh.

This is a cascode connection. A static bias voltage is applied to the gates of the high voltage switch 14 so that the low voltage switch 12 controls the high voltage switch 14 through voltage applied to the source. Cascode connection may avoid turn-on delay associated with the drain-gate Miller capacitance due to the static potential applied at the gate of the high voltage switch 14.

The low voltage switch 12 may trim the high voltage switch 14, such as by controlling the drive strength of the high voltage switch 14. The low voltage switch 12 may control the amount of voltage or current applied at the source of the high voltage switch 14 as a peak voltage. In the embodiment of FIG. 3, the low voltage transistors (e.g., low voltage switches M3/M4) are configured to trim the FETs (e.g., high voltage switches M1/M2) such that a drive strength of the FETs changes in response to the Low voltage transistor. The gate is connectable with the trim control connector 18 to set the trim level.

The trimming is provided without using additional high-voltage devices other than the one (unipolar) or two (bipolar) high voltage pulsers (switch 14). This may result in a more efficient integration due to the smaller size of low voltage switch 12.

The trimming controls the rise and/or fall time of the high voltage switch 14. The generated waveform may be created with programmable or set rise and/or fall characteristics. In the bipolar waveform generator embodiment of FIG. 3, the rise and fall times of the different type (P-type vs. N-type) of high voltage devices may be matched. By matching, the positive and negative pulses are more closely mirror images of each other. For harmonic or other imaging, the matched pulses may generate less transmitter based harmonic information, better isolating harmonic response from tissue or contrast agents. Where phase or pulse inversion is used to cancel fundamental response or where phase shifting is used to cancel other frequency components, matched pulses may better cancel the desired spectra.

In one embodiment, the low voltage switch 12 is part of an array of such switches. For example, FIG. 3 shows arrays of eight low voltage devices (switches M3/M4) connected in cascode with the FETs (switch M1/M2). The array of eight low voltage devices is binary-weighted in size to provide 256 effective combinations. The channel length of all eight devices is the same but the channel widths are in a ratio of 1:2:4:8:16:32:64:128. Other number of devices, channel length differences, and/or ratios may be provided. The low voltage switches 12 of the array are connected in parallel with each other.

The array of low voltage devices acts like a variable-strength switch. The exhibits variable on-resistance and variable peak current. During operation, there is a fixed dc voltage (e.g. 3.3V) between the high-voltage supply and the gate of the high-voltage transistor 14. This voltage is divided between the low voltage transistor array (e.g., CMOS devices) and the source-to-gate voltage of the high-voltage transistor 14. By varying the strength of the low voltage transistor array, more or less voltage can be applied as the source-to-gate voltage of the high-voltage transistor 14 thereby varying the strength of that fixed-size transistor. Separate gate signals are provided for turning on and off each of the low voltage switches 12 individually. In the example with eight switches 12 in the array, there are 256 levels of trimming provided. The switches 12 of the array are responsive to a digital control to turn on and off. In the bipolar example of FIG. 3, each of the arrays of low voltage switches M3/M4 is controllable by the digital code. The codes for the different arrays may be the same or different. The digital code indicates some of the CMOS devices to be on and some of the CMOS devices to be off during operation of the transmitter. The digital code controls an amount of trimming of the high-voltage switch 14. Since the low voltage switches 12 of the array turn the high voltage switch 14 on and off, the code indicates one group to be off during the pulsing and the other group to be both off before the pulse and on during the pulse.

By turning on a given group, a different level of trimming or strength control is provided. Different groups of Low voltage transistors may be selected for different purposes. For example, different groups with or without common switches 12 are used for pulsed wave operation and for continuous wave operation. The difference in peak amplitude or peak output current may affect the amount of trimming needed or desired. The Low voltage transistors that are on and off are different for the different peak or operating voltage levels. As another example, different transmitters 10 may have different characteristics due to manufacturing variance. By calibrating the transmitter 10, the group of low voltage switches 12 to use for a given application may be different for different transmitters.

The code may be used to turn the high voltage switch 14 on and off for generating a pulse. The selected group of low voltage switches 12 or a single low voltage switch 12 is turned on and then off to cause the high voltage switch 14 to turn on and off in cascode operation. The source of the high voltage switch 14 controls activation or the on/off state.

FIG. 3 shows an example control structure for trimming and operating the high voltage switches M1/M2. The bits received at the trim connectors trim_p/n select the low voltage switches M3/M4 to operate. This is a static selection, set for the duration of the generation of a transmit waveform for trimming. The trimming code used for a given operating point of the transmitter 10, such as the peak output current or the final on-resistance for a given application, is stored in the chip or off of the chip. In one embodiment, the code is stored in the chip after manufacture and measurement or calibration of the transmitter 10. The storage may be a fused-ROM or other type of memory. The code may be stored for use, or read out, interpolated and provided back to the chip.

The bit at each of the transmit control connectors 18 control the activation of the switch. In FIG. 3, the AND gates U5 and OR gates U10 output the digital code to the gates of the low voltage switches. The logic gates U5 and U10 are strength-adjusted according to the size of the M3/M4 low voltage device to which the logic gates U5 and U10 are connected respectively. For example, the logic gate attached to the 128x transistor M3 is a stronger gate than the one used for controlling the 1x M3 transistor. The AND gates U5 and OR gates U10 require both selection and activation of any given low voltage switch M3/M4 in the array to turn on the low voltage switches M3/M4. The inverters U3/U4 and U8/U9 form floating latches. These latches maintain the state (i.e., on or off) of the high voltage switches M1/M2. The state control is provided through floating capacitors C1-C4, reducing or eliminating any static supply current requirements. Reduction or elimination may minimize or reduce power dissipation.

In the example embodiment of FIG. 3, a fail-safe system is included. The transistors M5 and M6 form the fail-safe circuit. The drains are connected to the gate potential of the high voltage switches M1/M2 and the sources connect with the inverters U3/4, U8/9. The circuit forces the latches U3/U4 and U8/U9 to an off state at all times other than during transmission. The control signals for the fail-safe transistors M5 and M6 are either the same as the voltage at the gates of the high voltage switches M1/M2 (fail-safe off) or the same as the voltage supply (fail-safe on). A pair (positive and negative) of dc-coupled level translators provides the fail-safe control signal. This control sign switches between the two voltages (e.g., from +/−50 volts to +/−47 volts). The translators are either on or off the chip and may provide the signals in common to all of the transmitters 10 in the chip or in other chips. The power-up state of the transmitter 10 is with the fail-safe active to prevent simultaneous conduction in the positive and negative portions of the transmitter 10. Random power-on latch states may otherwise cause simultaneous conduction.

Other control circuitry, control signals, transmitter components, or arrangements may be used. Different combinations of components may be used on the same chip, spread between multiple chips, or provided as a circuit not integrated on a chip.

Figure 4:
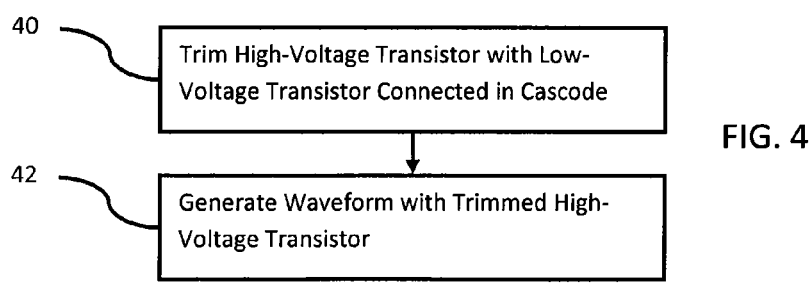
FIG. 4 is a flowchart diagram of one embodiment of a method for generating an ultrasound waveform.

FIG. 4 shows one embodiment of a method for generating an ultrasound waveform. The waveforms are either pulsed or continuous waves. Pulsed waves may have 1-5 cycles or more, and continuous waves may have 10 or more cycles (e.g., hundreds, thousands, millions, or billions of cycles). The method uses the transmitter of FIG. 1, FIG. 2, or FIG. 3, but other integrated circuits, chips, transmitters, waveform generators or devices may be used. Additional, different or fewer acts than shown in FIG. 4 may be provided.

In act 40, a drive strength of a high-voltage transistor is trimmed with a low-voltage transistor connected in cascode. The low-voltage transistor controls both the drive strength and the on/off operation or state of the high-voltage transistor.

For trimming, the low-voltage transistor controls the amount of source-to-gate (or gate-to-source) voltage applied to the high-voltage transistor. The trimming alters the drive strength. This alteration affects one or more properties of the operation of the high-voltage switch. The trimming may control the rise time, fall time, or both of the high-voltage switch. Trimming can also be used to control the on-resistance of the high-voltage switch. By adjusting the trimming, different rise or fall times of a generally square wave result.

For bipolar pulsing, different high-voltage transistors are trimmed differently or the same. The rise and fall times of positive and negative portions of the ultrasound waveform are matched using the trimming of the high-voltage transistors. Different low-voltage transistors in cascode with respective high-voltage transistors trim the output.

The amount of trimming is controlled by amount of activation or turn-on of the low-voltage transistor. One transistor may control the level over a range. Preferably, an array of of binary-weighed low-voltage transistors controls the trim levels. The control with an array may be digital. Each transistor in the array is turned all the way on or all the way off (digital control). The bits indicate which of the low-voltage transistors to contribute to the trimming and which do not. Some of the low-voltage transistors (e.g., CMOS devices) are activated or selected for activation and the others of the low-voltage transistors are deactivated or selected for not trimming. The selections for trimming are maintained during the generating of a given pulse, pulse sequence, or waveform.

Different selections may be used for different levels of trimming and/or different operating points of the transmitter. Different combinations of the low-voltage transistors are selected for different operating points. The peak amplitude to be used or operating point may determine the selection. The rise and fall time characteristics may be different for different levels of source voltage. As a result, the trimming to match the pulses or set the desired characteristic may be different. In one embodiment, different selection for trimming is used for different modes of imaging, such as different selections for pulsed wave, continuous wave, Doppler or flow, B-mode, elasticity, shear, strain, and/or contrast agent imaging modes. These or other modes may have different peak amplitude, rise and fall time, spectra or other requirements that may be controlled by trimming.

In act 42, the ultrasound waveform is generated. For unipolar waveforms, one high-voltage transistor as trimmed by the low-voltage transistor is cycled on and then off for each pulse. Two switches may be used in a unipolar transmitter, one to pull up and the other down (to zero). For bipolar waveforms, one high-voltage transistor as trimmed by a low-voltage transistor is cycled on and then off for each positive pulse. Another high-voltage transistor as trimmed by a low-voltage transistor is cycled on and then off for each negative pulse. Only the positive or negative operation may be trimmed in another embodiment. More than one high-voltage transistor may be used for generating the positive pulse and/or negative pulse.

The high-voltage transistor generates the pulse using the voltage applied to the source and gate. The source is trimmed by the low-voltage transistor. The low-voltage transistor applies the trimmed supply voltage to the source of the high-voltage transistor. The amount of trim or trim settings may be preprogrammed For example, different settings are used for different modes. The settings may be the same across all transmitters of a given type. Alternatively, each transmitter or batch of transmitters (e.g., transmitters from a same wafer or same run) is calibrated. The output waveform (or output current) is measured to determine an optimal or sufficient trim setting. This setting is stored in the chip or in another memory in an assembled ultrasound system. The calibration may be performed for each of the operating points.

The supply voltage is applied to the source of the low-voltage transistor. When the low-voltage transistor and high-voltage transistors are both on, the difference in voltage between the gate of the high-voltage transistor and the supply voltage at the source of the low-voltage transistor is below a break-down voltage level of the low-voltage transistor. For example, the difference is less than 4 volts for a CMOS device (e.g., low voltage transistor). Four volts may be the voltage tolerance of the low-voltage transistor, so exceeding four volts across the low-voltage transistor is avoided. Setting the gate voltage of the high-voltage transistor based on the voltage tolerance also biases the gate of the high-voltage transistor at a static or DC potential, avoiding or reducing turn-on delay. The gate voltage may vary during pulsing in other embodiments. The gate voltage may be different for different modes of operation or operating points, such as maintaining the amount of difference where the supply voltage is set based on the mode of imaging or desired peak amplitude of the generating waveform.

Since the low-voltage transistor is connected in cascode, the low-voltage transistor switches the high-voltage transistor on and off. The source voltage provided to the high-voltage transistor is controlled. For the array of trimming transistors, the selected transistors are turned on, causing a positive or negative voltage difference between the source and the gate of the high-voltage transistor. This voltage difference causes the transistor to conduct, generating the pulse. To turn the high-voltage transistor off, the source voltage is disconnected by the low-voltage transistors. Other pulsing control may be used.

When the high-voltage transistor is on or conducting, the source is connected with the output. This causes a high voltage (e.g., 10 volts or greater) pulse lasting until the high-voltage transistor is turned off. The generated pulse has a peak amplitude at the supply voltage level. Different supply voltages may be used to create different peak amplitudes.

The ultrasound pulses are output when generated. Continuous or pulsed waves are generated at different times but share a common output from the same integrated circuit and associated semiconductor chip. The same transmitter and associated waveform generator may be used for generating either pulsed waves or continuous waves for different modes of ultrasound imaging.

The rise and fall time of the positive pulses, negative pulses, or both are controlled by trimming. For harmonic and contrast agent imaging modes, multiple waveforms may be generated, but 180 degrees out of phase. By summing the received signals, the harmonic or other response of the tissue or contrast agent is provided. If the transmitted pulses include energy at the harmonic, a portion of the received signal at the harmonic will be due to transmission at that frequency rather than the nonlinear response of the tissue or contrast agent. By controlling the rise and fall time, less harmonic energy may be generated. By controlling the rise and fall time of the positive and negative pulses to be similar, better cancellation may be provided.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. In a bipolar transmitter for generating bipolar ultrasound pulses with first and second high-voltage transistors, an improvement comprising:

a first low-voltage transistor connected between a positive voltage source and a first source terminal of the first high-voltage transistor; and a second low-voltage transistor connected between a negative voltage source and a second source terminal of the second high-voltage transistor;

wherein the first and second low-voltage transistors are configured to adjust drive strengths of the first and second high-voltage transistors, respectively, and the first and second high-voltage transistors comprise first and second gates connected with positive and negative gate voltage sources, respectively, such that the first and second low-voltage transistors are operable to control an on/off state of the first and second high-voltage transistors, respectively, with the positive and negative gate voltage sources configured to maintain constant, during transmission, voltages connected to the first and second gates.

2. The bipolar transmitter of claim 1 wherein the first and second low-voltage transistors are connected in cascode with the first and second high-voltage transistors.

3. The bipolar transmitter of claim 1 wherein the first and second low-voltage transistors are each part of an array of CMOS devices connected between the positive and negative voltage sources and the first and second source terminals, respectively.

4. The bipolar transmitter of claim 3 wherein each of the arrays is controllable by a digital code indicating some of the CMOS devices to be on and some of the CMOS devices to be off during operation of the transmitter, the digital code controlling an amount of trimming of the first and second high-voltage transistors by the first and second low voltage transistors, respectively, the drive strengths set by the amount of trimming.

5. The bipolar transmitter of claim 4 wherein the first and second high-voltage transistors are operable with different voltage levels from the positive and negative source voltage sources, the CMOS devices that are on and off being different for the different voltage levels.

6. The bipolar transmitter of claim 1 wherein the first and second low-voltage transistors and the first and second high-voltage transistors are in an application specific integrated circuit (ASIC), the ASIC comprising inputs for connection to the positive and negative voltage sources, the positive and negative gate voltage sources, gate control signals for the first and second low-voltage transistors, and binary positive pulse and negative pulse activation.

7. The bipolar transmitter of claim 1 wherein the first and second low-voltage transistors are operable, through trimming of the first and second high-voltage transistors, respectively, with the drive strengths to match rise and fall times of pulses generated by the first and second high-voltage transistors.

8. The bipolar transmitter of claim 1 wherein the first and second low-voltage transistors comprise CMOS devices, the first high-voltage transistor comprises a P-type FET, and the second high-voltage transistor comprises a N-type FET.

9. The bipolar transmitter of claim 1 wherein the positive and negative gate voltage sources are within a low-voltage overload voltage of the first and second low-voltage transistors difference from the positive and negative voltage sources, respectively, during the transmission.

* * * * *